US005919645A

United States Patent [19]
Tung et al.

[11] Patent Number: 5,919,645
[45] Date of Patent: Jul. 6, 1999

[54] METHOD FOR THE DIRECT DETERMINATION OF THE TOXICITY OF PARTICULATE SOLIDS

[75] Inventors: Ker-Kong Tung, Del Mar; Charles Walbourn, Encinitas; Grace Scheibner, Oceanside, all of Calif.

[73] Assignee: Azur Environmental, Carlsbad, Calif.

[21] Appl. No.: 07/682,923

[22] Filed: Apr. 9, 1991

Related U.S. Application Data

[63] Continuation-in-part of application No. 07/577,933, Sep. 4, 1990, abandoned.

[51] Int. Cl.⁶ .................................................... C12Q 1/02
[52] U.S. Cl. .................................. 435/29; 435/32; 435/8
[58] Field of Search ................................. 435/29, 32, 8; 250/458.1, 261.2

[56] References Cited

U.S. PATENT DOCUMENTS

| | | | |
|---|---|---|---|
| 3,933,592 | 1/1976 | Clendenning | 435/8 |
| 3,958,938 | 5/1976 | Doonan et al. | 435/30 |
| 4,014,745 | 3/1977 | Fletcher et al. | 435/8 |
| 4,144,134 | 3/1979 | Plakas | 435/8 |
| 4,283,490 | 8/1981 | Plakas | 435/8 |
| 4,303,752 | 12/1981 | Kolchmainen et al. | 435/8 |
| 4,689,305 | 8/1987 | Stiffey et al. | 435/291 |
| 4,735,899 | 4/1988 | Stuart | 435/29 |
| 4,797,357 | 1/1989 | Mura et al. | 435/34 |
| 4,808,517 | 2/1989 | Blondini et al. | 435/4 |
| 4,847,197 | 7/1989 | Bansemir et al. | 435/32 |
| 4,950,594 | 8/1990 | Stiffey | 435/29 |

OTHER PUBLICATIONS

A Sediment–Contact Bioassay with Photobacterium Phosphoreum, Henry Brouer et al *Environmental Toxicology and Chemistry*, vol. 9 pp. , Pergamon Press.

Freshwater Sediment Toxicity Bioassessment: Rationale for Species Selection and Test Design, John P. Giesy and Robert A. Hoke, *J. Great Lakes Res.* 15 (4) 539–569; Internat. Assoc. Great Lakes Res. 1989.

Bulich "Bioluminscence Assays," Ch 4 57–74 in Biton & Dutka (Eds) Toxicity Testing Using Microorganisms vol. 1 CRC Press 1986.

Bitton CRC Critical Reviews in Env Control 13(1) 51–67.

Koopman Ch 5 123–25 in Dutka & Bitton (Eds) Toxicity Testing Using Microorganisms vo II CRC Press 1986.

*Primary Examiner*—Lora M. Green
*Attorney, Agent, or Firm*—Fitch, Even, Tabin & Flannery

[57] ABSTRACT

A method for the direct determination of the toxicity of a solid material by direct contact between the solid sample and a luminescent microorganism, consisting of the steps of forming a suspension of a luminescent microorganism in a 0.5% to 6% solution of NaCl or 20% solution of sucrose in distilled water diluent and contacting a sample of the solid to be tested directly with the suspension of luminescent microorganisms. A control including the microorganism in the diluent is also prepared. The combination of microorganism suspension and solid sample is incubated for a sufficient time to allow for the toxicity of the sample to affect the metabolism of the living organism. During or subsequent to the incubation period the combined organism and sample are subjected to a separation step to separate a major portion of the particulate solid from the suspension of microorganisms. The light output of the separated suspension is determined and compared with the light output of the control to arrive at the change in light output of the microorganism due to contact with the solid sample.

13 Claims, No Drawings

METHOD FOR THE DIRECT DETERMINATION OF THE TOXICITY OF PARTICULATE SOLIDS

RELATIONSHIP TO PENDING APPLICATIONS

This application is a continuation-in-part of application Ser. No. 07/577,933, filed Sep. 4, 1990 now abandoned.

FIELD OF THE INVENTION

The present invention relates to the detection of substances or conditions which are toxic to living organisms and more particularly to a method for the direct determination of the toxicity of particulate solids.

BACKGROUND OF THE INVENTION

Biological organisms are known to provide a sensitive and reliable indicator of the presence of even relatively small proportions of toxic substances in a fluid medium. Biological organisms which have been utilized as indicators of water toxicity include organisms such as daphnia, minnows and similar complex organisms. However, tests involving these organisms normally require a substantial amount of time, i.e. on the order of several days, in order to complete the toxicity determination. Methods employing contact between microorganisms, such as bioluminescent microorganisms, and a suspect substance, have been developed for the rapid determination of toxicity. By the use of bioluminescent microorganisms, a toxicity determination can be made in less than an hour as compared to the conventional toxicity determination, which may require several days to complete.

Regardless of the type of organism employed, acute water toxicity determinations conventionally measure the effect of a toxic substance or a condition in the water on the metabolism of a living organism. A number of established test methods employing various living organisms are available. However, testing the toxicity of particulate solids such as soils, sediments, sludge and other similar particulate solid materials, has presented a problem in that such materials cannot rapidly and reliably be tested for their toxicity. Solid materials are conventionally tested by indirect methods, which utilize a solvent or acid to extract the toxic substance from the particulate solid. The solvent containing the toxic substance is then treated as necessary and tested against a living aquatic organism. It will be apparent that with any indirect method, the organism is not directly in contact with the solid sample, and this lack of direct contact may produce erroneous results. For example, with acid extraction the soil particles may be partially decomposed, and heavy metals, which are normally part of the composition of a soil, but which are not readily water soluble, may be extracted. The resultant toxicity of an acid extract may be greatly enhanced compared to that for natural leachates of the same sample. In such cases, an acid extract from a sample for which the natural leachate would be virtually non-toxic (because the slight water solubility of the metal compounds present makes them biologically unavailable to aquatic organisms) may provide a false positive indication of toxicity. In addition, indirect methods can produce erroneous results due to operator error resulting from the number of steps and chemical treatments that must be carried out before the liquid can be brought into contact with a living organism.

To avoid some of the foregoing problems, direct methods employing benthic organisms have been utilized to directly test the toxicity of a solid material. Benthic organisms are defined as those organisms which can be found at the bottom layers of ponds, lakes and the like or which normally dwell in association with a sediment or soil. Benthic organisms used in recent years for soil and sediment toxicity testing include various complex organisms such as earthworms, nematodes, oyster larvae, clam larvae and the like. Benthic organisms can be difficult to grow and harvest in sufficient quantity for reliable and reproducible test results, the tests are labor intensive (at the beginning and end) and the required test times are long. For these reasons, only one concentration of sample (100%) is normally tested using benthic organisms.

In summary, neither the direct (benthic organisms) nor the indirect methods (extracts and elutriates) are entirely satisfactory for all purposes. The choice of test methods depends largely on the question to be answered. Water elutriates cannot determine the total amounts of sparsely soluble toxic substances present in the solid phase, while organic solvent extraction and acid solution of the solids can, if and when the extracted toxicants do not precipitate when added to an aqueous test solution. Therefore, the combination of organic solvent and acid extractions gives a better indication of total toxic matter present, if and when that is the concern. However, they yield no information with regard to bioavailability of the toxicants in the original sample. Water elutriates yield the most relevant results with regard to the potential impact of leachates on aquatic organisms, while direct toxicity determinations employing benthic organisms yield results which are much more indicative of bioavailability to benthic organisms. However, as noted above, tests with benthic organisms are slow, and it is difficult to obtain reproducible results between different laboratories which must grow their own stock.

SUMMARY OF THE INVENTION

It is an object of the present invention to provide a direct method for the determination of the toxicity of particulate solids.

Another object of the invention is to provide a rapid and cost-effective method for the direct test of soils, sediments and sludge for toxic substances or toxic conditions employing living organisms.

These and other objects and advantages are achieved by the method of the present invention which comprises forming a suspension of a luminescent microorganism in a non-toxic liquid and contacting a particulate sample of the solid to be tested directly with the suspension of luminescent microorganisms. The combination of microorganism suspension and solid sample is incubated for a sufficient time to allow for the toxicity of the sample to affect the metabolism of the living organism. Subsequent to a timed contact between the suspension and the solid sample, the combined organism and sample is subjected to a separation step to separate a major portion of the particulate solid from the suspension of microorganisms. The separation step may include centrifugation, or, preferably, filtration after incubation. It has been found that merely allowing the combined organism and suspension to stand without agitation during the incubation period will separate a major portion of the solid particles of the sample from the suspension. The light output of the filtrate is determined and compared against that of a control suspension of the microorganisms (which has been treated as the other except with regard to combination with the solid sample) to arrive at the change in luminescence due to contact of the microorganisms with the particulate solid sample.

By making a plurality of serial dilutions of the combined sample and microorganism suspension, a dose-response curve can be developed for the determination of the EC50 which is defined as that concentration (e.g. in parts per million, PPM) of the sample required to reduce the light output of the microorganism by 50%. The EC50 is the commonly reported result of such toxicity testing.

Other objects, advantages and features of the present invention will become apparent from the detailed description of the invention which follows.

DETAILED DESCRIPTION OF THE INVENTION

The invention provides a method for the direct determination of the toxicity of particulate solid materials using bioluminescent microorganisms as a living, biological indicator. The term particulate solid material includes soils, sediment, sludge, drilling mud and the like for which a rapid, easy and inexpensive method for the determination of the toxicity of that material is desired. For example, drilling muds must be tested for their toxicity prior to disposal because of the additives that are introduced to the drilling mud during the drilling process. Spent sludge from sewage treatment plants and the like should be routinely tested for toxicity before disposal in land fills or other disposal areas. Similarly, sediment from the sea, lake or pond bottoms, river beds and the like must often be tested for toxicity before dredging operations, or following an environmental accident such as an oil spill or the like.

For cost effective and rapid determinations microorganisms such as bacteria and the like have shown advantage over the more complex organisms conventionally used as the living organism for toxicity determinations. A highly successful protocol involving the use of bioluminescent microorganisms has been developed and is marketed under the trademark Microtox by Azur Environmental, Carlsbad, Calif. The Microtox toxicity determination system is based on the use of bioluminescent microorganisms, the light output of which is directly effected by the metabolism of the organism. Contact with toxic materials adversely affects the metabolism of the microorganism and produces a reduction in light output. The light output reduction for a plurality of sample concentrations can be used to determine the EC50 of the sample for the microorganism. The Microtox system is rapid, on the order of five to thirty minutes, and is highly suited for field work and on-site work away from the laboratory, particularly in view of the fact that the microorganisms can be reduced to a nascent state, such as by lyophilization, and can be easily reconstituted to their viable state at the test site. Since the organisms are cultured and processed at a central location, reproducibility and control of the test organisms, and thus the test results, can be readily achieved, much in the nature of a chemical test using reliably manufactured chemical reagents.

Tests involving microorganisms, such as the MICROTOX® toxicity determination method have been generally thought to be unsuited for direct testing of particulate solid material for several reasons. For example, in a direct test using microorganisms, it would be expected that the contact period would be many hours, which far exceeds the published stability of the reconstituted luminescent microorganisms. The long exposure period would be expected in view of the fact that experience with the indirect methods indicates that water extraction leach rates are very low and require a substantial amount of time to leach a discernable amount of toxic material from the solid particles. Of course this is one of the reasons why the toxicants of greatest concern in soils and sediments are the so-called "persistent" materials, i.e. those which will not leach out rapidly from the solid material but which remain as a source of toxicity for months, years or decades. Yet another reason is that the microorganisms tend to absorb, or attach to, particulate matter, resulting in losses of microorganisms during separation by both settling and filtration. Because of the "shadowing" effect by particles remaining in solution, positioned between the microorganisms and the photon detector, or to which a microorganism is directly attached, a reliable determinination of the light output of the microorganisms when comingled with solid particles of totally unknown size, shape and physical/chemical composition would not be considered to be feasible by those skilled in the relevant arts. More specifically, when solid particles are co-mingled with light emitting microorganisms, those skilled in the relevant arts would expect the observed light output to depend upon a complicated function of the size, shape, optical properties, the electrical charge on, and other physical and chemical properties of the particles, all of which properties are involved in both direct optical interference and in the tendency of microorganisms to bind. The light output of the microorganisms would be expected to depend on the type and concentration of particles present, as well as upon the microorganism's toxic response. Therefore, from the most elementary considerations, the loss of light due to absorption of microorganisms on the solid phase during separation and due to interference by those particles remaining in suspension, would be expected to largely mask the toxic effect being measured. While the effects described do cause a significant interference when the actual toxicity is low, comparison of the results obtained for each sample tested to those for a simular reference sample permits one to rank each sample with regard to toxicity.

It has been unexpectedly found, therefore, that luminescent microorganisms can be directly co-mingled with particulate solid material and serve as a reliable biological indicator of the toxicity of the particulate solid material with which it is co-mingled. Based upon test results discussed below in connection with several specific examples, toxicity determinations made in accordance with the method of this invention either directly correlate with the standard indirect extraction methods, or, for toxicants which are relatively insoluble in water, the method of this invention provides higher sensitivity.

As the biological indicator in the method of the present invention it is highly preferred to utilize one of the several strains of marine bacteria which are known to exhibit strong luminescence in the course of their growth cycle. Such strains of luminescent bacteria include the Photobacteria such as *P.splendidium, P. mandapamensis,* and *P. phosphoreum*. Strains of bacteria from the genus Vibrio, such as, for example, *V.fischeri*, as well as microorganisms from the genus Lucibacterium such as *L. harveyi* and *L. achromobacter*, likewise exhibit luminescence. All specific example test results discussed below were obtained using *P. phosphoreum* (NRRL B-11177) from Microbics Corporation lyophilized reagent, but other microorganisms may also be used in the practice of this invention, as enumerated above and in the following paragraph.

In addition to the various bacteria, other types of microorganisms also exhibit luminescence such as, for example, certain marine dinoflagellates, which notably include Noctiluca and Gonvaulax. In addition, certain varieties of fungi (Basidiomycetes) also exhibit luminescence, including, for example, *Armillaria mellea, Panus stipticus, Mycena poly-*

*gramma* and *Omphalia flavida*. Luminescent bacterial and fungal microorganisms are available from the American Type Culture Collection, 12301 Parkland Drive, Rockville, Md., or Northern Regional Research Laboratories, U.S. Dept. of Agriculture, Peoria, Ill., as well as from many commercial and university laboratories.

Typically, the stock cultures of the microorganism are grown from a preserved culture by transferring a portion of the cells from the preserved culture to a nutrient medium where they are permitted to grow and multiply. The choice of medium used for growing the culture is dependent upon the type of culture being employed and the manner in which the microorganisms are to be subsequently treated in preparation for their use in the present invention.

A preferred growth medium for the more common luminescent microorganism is an agar containing between about 0.25% and about 0.7% of sodium or potassium pyrophosphate, about 0.5% glycerol, between 0.5% and about 1% peptone (animal and/or vegetable), up to about 1% hydrolyzed casein and about 0.5% to about 6% of sodium chloride; the remainder being water. The pH of the growth medium preferably ranges between 6.5 and about 7.5 and most preferably is on the order of 7.0. For marine microorganisms, seawater can be substituted for the water in the nutrient medium, and the sodium chloride omitted. Also depending on the strain of microorganism being grown, an extract such as meat extract, squid or fish extract can be highly beneficial in the nutrient medium.

After culturing, a small portion of the microorganisms are suspended in a clear non-toxic liquid for subsequent contact with the sample being tested. For reproducibility and reliability of results it is highly preferred that the microorganisms be cultured at a central location and distributed to the various test sites. In this connection it is highly preferred to lyophilize test quantities of the microorganisms so that they can be retained in a nascent lyophilized condition until ready for use. The lyophilized microorganisms can be packaged in the proper quantity and shipped to a test site. The prepackaged lyophilized microorganisms are readily reconstituted to a viable condition by the addition of distilled water, when they have been lyophilized in an inert liquid having a sufficient osmolality so that the microorganisms suspended therein do not lyse. When the reconstituted microorganisms are diluted for testing the diluent employed must also provide adequate osmotic protection. Good results have been obtained with marine microorganisms by using a solution of between 0.5% and 6% NaCl in distilled water, or a solution of 5% to 36% sucrose in distilled water, which has corresponding osmolality.

The concentration of microorganisms used in the test suspension is a matter of choice. For example, the upper limit is about $10^7$/mL for resting *P. phosphoreum* cells, to avoid oxygen depletion during the test (which can reduce the light produced by the microorganisms), while the lower limit on microorganism concentration is determined by the intensity of light output (base line output) required for an acceptable photometer signal-to-noise ratio. Good results are obtained with a *P. phosphoreum* concentration of about $2 \cdot 10_6$/ml. In forming the test suspension, the lyophilized *P. phosphoreum* are first reconstituted with distilled water at a concentration of about $10^8$/mL, and then diluted to 50 ml in a 0.5% to about 6.0% NaCl in distilled water diluent solution (or equivalent osmolality of sucrose) to provide the preferred cell concentration of about $2 \times 10^6$/ml. It should be noted that the distilled water, with and without concentrations of sodium chloride or sucrose, utilized for reconstitution and for dilution purposes, respectively, should be pretested to insure that it is non-toxic and does not affect the test results. Lyophilized luminescent microorganisms and the non-toxic solutions are available from Microbics Corporation, Carlsbad, Calif. It should be clearly understood, however, that the microorganisms can be cultured at the test site using methods well known in the art.

In carrying out the test in accordance with the invention, it is preferred to directly mix the sample in a predetermined volume of the stock suspension of the microorganisms, referred to herein as stock solution, and to thereafter make a series of serial dilutions of the sample in the stock solution for ultimately preparing a dose response curve. In addition, a reagent blank consisting only of the predetermined volume of the stock solution is prepared. After combining the sample (including dilutions, if any) with the stock suspension of luminescent microorganisms, the combined sample and suspension are maintained in contact for a period of time sufficient to permit the microorganisms to be affected by any toxic substance which may be contained in the solid particles but for a short enough period of time to maintain adequate stability of the light output of the unexposed (i.e. control) microorganisms. Good results have been achieved with *P. phosphoreum* when contact is maintained for about twenty minutes. However, depending upon experience, it may be found that the contact period can be advantageously shortened or lengthened, particularly for specific applications, without effecting the rank order of the test results obtained for a given set of samples.

At the end of the contact period, the sample/microorganism combination is subjected to a filtration step in order to eliminate a major portion of the solid particles from the microorganisms and liquid. The type of filtration is not critical although the pore size of the filter must be large enough to permit the microorganisms to pass (about 2 microns or larger) while screening out a major portion of the solid particles larger than about 50 microns. In the examples, cited below, the filters had a pore size of about 35 microns, and those particles remaining in suspension after a 20 minute incubation, and also passing through the filter, had no discernable effect on the test results. Since the sample aliquots tested are rather small, excellent results have been achieved using a commercially available filtering system developed for the separation of blood serum from clotted or centrifuged blood cells. In this system, the filter (about 35 micron) is sealed to and forms the head of a tubular plastic piston (or column), which is formed with a flexible seal ring adjacent to the end mounting the filter. The seal ring seals against the wall of a standard disposable plastic blood collection tube. The microorganisms are combined with the particulate solid in tubes which match the filter columns and filtration is accomplished by gently pressing the filter column downward. The filtrate containing both the unbound microorganisms and those bound to the small particles still in suspension rises in the inner chamber, while solid particles significantly larger than bacteria, and bacteria which are bound to such larger particles, remain below the filter. Filtering systems of the type described are marketed under the trademark SERA-SEPARA™ by Evergreen Scientific, P.O. Box 58248, Los Angeles, Calif. 90058.

After the contact and filtering steps, the light output from the filtrate is determined. For this purpose any conventional light sensing means can be employed to read the light output from the filtrate. These devices normally incorporate a photo multiplier tube (PMT) as the device for indicating the intensity of the light. A suitable instrument is described and claimed in the U.S. Pat. No. 4,213,703, granted Jul. 22, 1980 to Haunold et al. An instrument of the type described therein is manufactured and sold by Azur Environmental, Carlsbad, Calif. as the MICROTOX® Model 2055 Toxicity Analyzer. It will be understood that fine particles (less than 35 microns in the examples discussed below) of the sample which do not settle out during the incubation period may pass through the filter during the filtration step and be present in the filtrate. Surprisingly, these particles have little or no effect on the test results, as shown by the examples discussed below.

It should also be noted that the temperature of the suspension of microorganisms will affect both the sensitivity and the actual light output of the microorganisms in the suspension. Accordingly, it is preferred to run all determinations at the same temperature to insure reproducibility of results. Good results are achieved with a range of temperatures of from about 10° C. to about 30° C. The preferred test temperature will be that temperature at which maximum change in light output is recorded. This may depend upon the nature of the sample being tested and the type of toxicant which may be encountered. Thus, the temperature at which the determination is to be made is a matter of choice, and for most purposes incubation can be carried out at room temperature. In any case, the temperature of the filtrate, the light output of which is to be read, should be permitted to stabilize at a fixed temperature before recording the light output.

The invention is further described by the following examples which are illustrative of specific modes of practicing the invention and are not intended as limiting the scope of the invention as defined by the appended claims.

EXAMPLE 1

The following sets forth a typical assay protocol for the direct determination of the toxicity of particulate solids in accordance with the present invention.

Ten 15.5 mm by 56 mm test tubes were carefully cleaned and rinsed in non-toxic distilled water and labeled 1–10. The solid particulate sample was mixed thoroughly to ensure a homogenous distribution of the various sized particles in the sample.

A stock suspension of microorganisms was prepared by adding 1 ml of distilled water to a pellet of lyophilized *P. phosphoreum* to form a concentrated suspension. The concentrated suspension was diluted to 50 ml with a solution of 2% sodium chloride in distilled water at room temperature to give a stock solution cell concentration of about $2\times10^6$/ml. To nine test tubes numbered 2–10 were added 2 ml of the stock solution. 0.4 gm of the sample was weighed out and transferred to a test tube identified as No. 1, and 4 ml of the stock solution was added. The suspensions in the test tubes were all at ambient temperature. For preparing a doseresponsive curve, serial dilutions were made from test tube No. 1 by transferring 2 ml of the combined microorganism and sample suspension to test tube No. 2. The combination in test tube No. 2 was thoroughly mixed and 2 ml were transferred from test tube No. 2 to test tube No. 3. This procedure was followed to test tube No. 9. No transfer was made to Test tube No. 10 which consisted solely of the stock solution, to serve as a reagent control. During the transfer/dilution steps the suspension and sample were thoroughly mixed, which ensured contact between the microorganisms and the particles of the sample, as well as uniformity of the combined suspension being transferred. The microorganisms and particulate sample were maintained in combination for 20 minutes at ambient temperature.

Following the 20 minute incubation period, the contents of each of the test tubes were subjected to a filtration step utilizing filter columns distributed under the registered trademark SERA-SEPARA™ by Evergreen Scientific, Los Angeles, Calif. The pore size of the filter was about 35 micrometers. 0.5 ml of the filtrate from each filter column was transferred to a corresponding cuvette in the incubator of a Microtox® model 2055 toxicity analyzer, at 15° C., for the determination of the light output. After transfer to the Microtox® Analyzer incubator, approximately 5 minutes were allowed before taking any readings to assure thermal equilibration. The determination of the light output from each sample was then made, using the Microtox® model 2055 toxicity analyzer as described above. Cuvette No. 10, the reagent control, was read first to determine the baseline light output from the stock solution (microorganism suspension). Following that, light output readings were recorded for each of cuvettes 1–9 and the toxic responses were calculated using the control light output to normalize that from each of the other cuvettes, as described in the model 2055 Microtox® toxicity analyzer instructions. A log-log graph of concentration of particulate solid vs. normalized reduction in light output was used to determine the EC50 concentration for the sample.

EXAMPLE 2

The toxicity of various particulate solid samples was determined in accordance with the protocol described in Example 1 and the toxicity determinations were compared with toxicity determinations made utilizing indirect methods. The solid samples included synthetic analytical research matrices (SARM) prepared for the Environmental Protection Agency by EPI Associates under contract No. 68-03-3413. The SARMS are surrogate test soils prepared to resemble typical soils found at so-called "superfund sites". Uncontaminated soils (including 30% clays, 25% silt, 20% sand, 20% top soil and 5% gravel) were selected and blended to create a typical uncontaminated soil, referred to as "clean SARM", or SARM. Four levels of typical contaminants found at superfund sites were added to SARM to prepare SARM I through SARM IV, as typical contaminated soils. The target concentrations of toxic materials in the four SARM formulations are set forth in Table I.

TABLE I

TARGET CONTAMINANT CONCENTRATIONS FOR SARMS (mg/kg)

| Added Toxicant | SARM I High Organic Low Metal | SARM II Low Organic Low Metal | SARM III Low Organic High Metal | SARM IV High Organic High Metal |
|---|---|---|---|---|
| VOLATILES | | | | |
| Acetone | 6,800 | 680 | 680 | 6,800 |
| Chlorobenzene | 400 | 40 | 40 | 400 |
| 1,2-Dichloroethane | 600 | 60 | 60 | 600 |
| Ethylbenzene | 3,200 | 320 | 320 | 3,200 |
| Styrene | 1,000 | 100 | 100 | 1,000 |
| Tetrachloroethylene | 600 | 60 | 60 | 600 |
| Xylene | 8,200 | 820 | 820 | 8,200 |
| SEMIVOLATILES | | | | |
| Anthracene | 6,500 | 650 | 650 | 6,500 |
| Bis(2-ethylhexyl-phthalate | 2,500 | 250 | 250 | 2,500 |
| Pentachlorophenol | 1,000 | 100 | 100 | 1,000 |

TABLE I-continued

TARGET CONTAMINANT CONCENTRATIONS FOR SARMS (mg/kg)

| Added Toxicant | SARM I<br>High Organic<br>Low Metal | SARM II<br>Low Organic<br>Low Metal | SARM III<br>Low Organic<br>High Metal | SARM IV<br>High Organic<br>High Metal |
|---|---|---|---|---|
| INORGANICS | | | | |
| Arsenic | 10 | 10 | 500 | 500 |
| Cadmium | 20 | 20 | 1,000 | 1,000 |
| Chromium | 30 | 30 | 1,500 | 1,500 |
| Copper | 190 | 190 | 9,500 | 9,500 |
| Lead | 280 | 280 | 14,000 | 14,000 |
| Nickel | 20 | 20 | 1,000 | 1,000 |
| Zinc | 450 | 450 | 22,500 | 22,500 |

In addition to three of the SARM samples, several test samples obtained from actual sites were subjected to toxicity determinations in accordance with the present invention (direct) and by indirect (extraction) methods. The additional test samples include samples taken from two points of a harbor bottom in Indiana and identified as IHC 3 and IHC 4. The toxicity of each sample was determined in duplicate by each of three methods: the assay protocol of Example 1; an indirect method employing an aqueous (2% NaCl in distilled water) elutriate; and an organic solvent (methylene chloride) extract. The toxicity determinations for all three methods were made using Microbics Corporation reagent, which contains lyophilized *P. phosphoreum*, NRRL B-11177. The light output readings were made using a Microtox® 2055 analyzer for both the direct and the indirect methods.

The mean values of the results of the duplicate toxicity determinations by each method are set forth in Table 2 below.

TABLE 2

TOXICITY DETERMINATION (EC50, IN PPM)

| | TOXICANTS ADDED | | INDIRECT METHODS | | DIRECT METHOD |
|---|---|---|---|---|---|
| SAMPLE | ORG. | INORG. | *ORGANIC SOLVENT | *AQUEOUS SOLVENT | |
| SARM | 0 | 0 | NONTOXIC | NONTOXIC | 20,550 |
| SARM II | LOW | LOW | 7,580 | 4,930 | 5,450 |
| SARM III | LOW | HIGH | 57,000 | 530 | 18 |
| SARM IV | HIGH | HIGH | 488 | 200 | 10 |
| IHC3 | UNKNOWN | | — | 21,400 | 2,610 |
| IHC4 | UNKNOWN | | — | 23,500 | 2,300 |

*The organic solvent was methylene chloride, evaporated after extraction to reduce the methylene chloride volume. The residual was then resuspended in dimethyl sulfoxide (DMSO) for testing, to reduce the solvent toxicity effect of methylene chloride.
*The aqueous solvent was 2% NaCl in distilled water.

The results in Table 2 are reported as parts per million (PPM) of the solid sample required to reduce the light output of the microorganisms by 50%. This figure, in PPM, is referred to herein as the EC50 value. It will be evident that the higher the EC50 value, the less toxic the substance or condition.

Experience with the method of this invention has shown that EC50 values of about 20,000 and higher are normal for clean soils (i.e. uncontaminated soils). In a binary ranking system, therefore, samples having EC50 values of 20,000 PPM or higher could be considered to be non-toxic, and those having an EC50 less than 20,000 PPM could be considered to be toxic. It will be apparent from a review of Table 2 that the rank order of the EC50 values obtained with the direct method of this invention corresponded with the EC50 rank order obtained using the indirect (solvent extraction) methods. Furthermore, it is apparent that the method of this invention provided either approximately equal or lower EC50 values (i.e. higher toxicity) for all samples.

Reviewing the results in Table 2 in greater detail, it will be seen that SARM II, which contains low concentrations of both organic and inorganic (metal) toxicants, is about 50% more toxic by the method of this invention than it is to the organic solvent extract, and equally toxic (within the precision of the test) to the 2% NaCl elutriate. Apparently, as one would expect, the organic solvent did not remove the inorganic toxicants. By comparison to the result for the aqueous elutriate of SARM II it is also apparent that there was no significant interference from the direct co-mingling of the bacteria with the solids, by loss of bacteria in the separation step, or due to residual suspended particulates at the time the light readings were taken, both of which factors are potential problems when practicing this invention.

The results for SARM III, which had low organic and high inorganic (metal) target concentrations, showed it to be less toxic than the clean soil (from which it was made) when the organic solvent extract was tested. It is probable that the steps of evaporating the methylene chloride extractant and resuspending in DMSO resulted in loss of the volatile and semivolatile organics which were added in low concentration to make SARM III, and the organic solvent would not be expected to extract the inorganic toxicants. This result thus illustrates the potential hazards of testing organic extracts which were mentioned above. Because the solid particles were not carried over in the extractant, the fact that the it was less toxic than was the clean SARM by the method of this invention could mean that a significant loss of bacteria with the settled and filtered clean SARM may have caused a significant portion of the observed toxic response shown in Table 2. However, it is also possible that the clean SARM actually does contain insoluble inorganic toxicants which are bioavailable when tested in accordance with the method of this invention.

SARM III was found to be highly toxic with the aqueous extraction method, while by the direct method of the present invention the material was found to be extremely toxic, which is in keeping with the list of materials added, given in Table 1. A similar result was achieved with SARM IV, which had high concentrations of both organic and inorganic materials. Specifically, both indirect methods (extractions) show SARM IV to be highly toxic, while the direct method of this invention shows it to be extremely toxic. Clearly, the increase in toxic response observed when practicing this invention (greater than twenty-fold for SARM III and SARM IV) is not simply the sum of the responses observed with the two indirect methods. Neither can this enhanced response be attributed to the possible artifacts of the new method, in view of the results achieved on the clean soil (SARM) and on SARM II, discussed above, since all of the SARMs consist of the same clean soil with varying amounts of added toxicants.

Finally, it may be seen that the IHC samples were both relatively non-toxic to the aqueous extraction, while, by the direct method, both samples were determined to be definately toxic. (No organic solvent extract was made on these samples on the advise of the laboratory which provided them, because the samples were so old it was considered to be improbable that the organic content had not changed drastically.)

The results of this example indicate that with indirect (organic solvent extraction) methods it is possible to inadvertently run the wrong type of extraction and achieve a determination which would indicate that the material is nontoxic. However, with the direct method of this invention such inadvertency is avoided.

EXAMPLE 3

The following example illustrates the effect of the temperature during the period of contact between the particulate solid material and the microorganisms upon the EC50 values. Samples were selected from the particulate solid materials identified as SARM I, SARM II, MERCO I and IHC 3. The samples were run in accordance with the assay protocol as set forth in Example 1, except that contact between the microorganisms and the solid sample was maintained at three different temperatures; 15° C., 25° C., and 30° C. The results are set forth in Table 3.

TABLE 3

EFFECT OF CONTACT TEMPERATURE

| SAMPLE | NO. OF TESTS | CONTACT TEMPERATURE | | |
|---|---|---|---|---|
| | | 15° | 25° | 30° |
| | | EC50 (PPM) | | |
| SARM I | 2 | 565 | 890 | 1,045 |
| SARM II | 6 | 3,724 | 4,911 | 4,240 |
| MERCO 1 | 2 | 29,000 | 19,020 | 20,500 |
| IHC 3 | 2 | 1,890 | 2,050 | 1,900 |

An acceptable precision for biological determinations of the type to which the present invention relates is about 20%, at the very best. From the results set forth in Table 3 it can be concluded that although there may have been some effect of contact temperature in the range of 15° C. to 30° C., the effect is within the precision of such tests, and it can therefore be concluded that the contact temperature between the microorganisms and the particulate solid (so long as maintained at a viable range of the microorganism) is not significant.

EXAMPLE 4

In the case of particulate solid materials, it is wellknown that some toxic substances are more tightly absorbed to particles than others. In addition, solubility rates generally increase when the solvent/solute mixture is agitated. It would be expected, therefore, that agitation of the combined microorganism and particulate solid would have an important affect on the outcome of a toxicity test using the method of this invention. The following example demonstrates the effect that agitation of the combined microorganism and particulate solid has upon EC50 values. The assay protocol was as set forth for Example 1 except that duplicate determinations were run on each sample; one determination being conducted as in Example 1 with no agitation during contact between the microorganism and the particulate solid and one determination made in which the combined microorganism/particulate solid was subjected to continuous shaking at 200 RPM on a vortexing mixer during the twenty minute contact. The results are set forth in Table 4.

TABLE 4

EFFECT OF AGITATION ON MEAN EC50

| SAMPLE | NO OF TESTS | EC50 NOT AGITATED | EC50 AGITATED |
|---|---|---|---|
| SARM | 2 | 20,550 | 8,580 |
| SARM I | 2 | 926 | 910 |
| SARM II | 3 | 5,290 | 1,660 |
| SARM III | 2 | 6 | 6 |
| MERCO 1 | 5 | 19,000 | 11,430 |
| IHC 3 | 2 | 2,060 | 1,050 |
| IHC 4 | 2 | 2,400 | 1,450 |

As might be expected, some EC values are lower, that is tending more towards toxicity, for the determinations which involved agitation during the contact period. However, taking the corresponding EC50 value for SARM (clean soil) as the threshold toxicity value for the results, it will be seen that the relative toxicity rankings for the samples tested remain the same with and without agitation.

EXAMPLE 5

In the assay protocol of Example 1 it will be noted that the particulate solid sample is introduced to a test tube which contains a microorganism suspension and thereafter serial dilutions are made, first by transfer from the test tube containing the sample suspension at its highest concentration into a tube containing the same concentration of microorganisms, then by repeating this step for each succeeding test tube. This raises the question as to whether the carryover of 50% of the microorganisms from each tube into the next tube will bias the resulting toxicity determination toward higher toxicity. In fact, after the dilutions have been made, 50% of the microorganisms in each tube will have been exposed to the next higher concentration of particulate solids briefly, 25% will also have been exposed to the second higher concentration, etc. One thirty-secondth of the microorganisms in the fifth dilution, for example, will have been briefly exposed to the maximum concentration of solid particulate sample. The potential bias in the protocol of Example I was, therefore, investigated.

Determinations were made using samples of SARM I, SARM II, Merco 1 and IHC3. Two sets of determinations were made for each of the materials. One set of determinations was made in accordance with the protocol of Example 1, without agitation and using the serial dilution procedure described therein (the biased method). The second set of determinations (the unbiased method) was also run as described in Example 1 but the sample dilution procedure was carried out as follows: Two milliliters of diluent solution (2% NaCl in distilled water) were added to test tubes numbered 2 through 10. 0.4 grams of the solid to be determined were weighed into test tube No. 1 and 4 ml of the diluent solution (2% NaCl) were added. The contents of test tube No. 1 were thoroughly mixed and 2-fold serial dilutions were prepared by transferring 2 ml of the suspended solids from test tube No. 1 to test tube No. 2. After thorough mixing 2 ml were transferred from test tube No. 2 to test tube No. 3. This two-fold serial dilution scheme was continued to test tube No. 9, in which case the 2 ml aliquot removed from test tube No. 9 was discarded. Test tube No. 10 contained 2 ml of the diluent solution as a reference for the base line reading. A 40 microliter aliquot of the concentrated suspension of bacteria, prepared in accordance with Example 1, was added to the tubes in the sequence 10 through 1. With this procedure, the need for preparing the stock solution (suspension of microorganisms) used in Example 1 is avoided. After addition of the concentrated microorganism suspension the contents of the test tubes were thoroughly mixed as previously described and contact was maintained without agitation for a period of twenty minutes at room temperature. Following the contact period the larger particulate solids were filtered from the liquid phase and the light outputs of the filtrates were determined, as described in Example 1, in the same sequence in which the microorganisms were added, 10 through 1. (The low-to-high concentration sequence reduces the effects of toxicant carryover when pipette tips are not changed after every transfer, and using the same sequence keeps exposure time for all cuvettes approximately equal.) The results are set forth in Table 5 below.

TABLE 5

EFFECT OF SAMPLE DILUTION METHOD

| SAMPLES | NO. OF. TESTS | EC50 BIASED | EC50 UNBIASED |
|---|---|---|---|
| SARM I | 3 | 600 | 527 |
| SARM II | 9 | 2,900 | 4,200 |
| MERCO 1 | 3 | 15,360 | 18,100 |
| IHC | 3 | 2,970 | 3,580 |

From the results reported in table 5 it can be concluded that there is no significant difference between the two protocols, at least for the samples tested. It is preferred to utilize the procedure of Example 1, therefore, because it saves test time by eliminating one liquid addition and one mixing step for each test tube. It should be pointed out, however, that the unbiased method more closely parallels the established indirect protocols using the Microtox® system and thus may be preferred by those who routinely perform either normal Microtox® acute water toxicity tests, or indirect procedures on elutriates or pore water.

From the foregoing it will be seen how the advantages of the present invention are achieved by the various embodiments and modifications described in the foregoing description and examples. Further modifications will be apparent to those skilled in the art. Such modifications are included within the scope of this invention as defined by the following claims.

Having described the invention, we claim:

1. A method for the direct determination of the toxicity of particulate solid material comprising the steps of:
   a. forming a suspension of a viable luminescent microorganism in a non-toxic liquid having sufficient osmolality to avoid lysing of said microorganism therein;
   b. directly combining a known quantity of a particulate solid material sample and a predetermined volume of said microorganism suspension for direct contact between said microorganism and said particulate solid sample;
   c. preparing a control comprising said microorganism suspension without any of said particulate solid material;
   d. incubating said combined particulate solid material sample and microorganism suspension for a predetermined time;
   e. separating a major portion of said particulate sample from said suspension of microorganisms;
   f. separately reading the light output emitted by said microorganisms in said separated suspension and by said microorganisms in said control; and
   g. comparing said light output of said separated suspension to the light output of said control to determine the change in light output as an indication of the toxicity of said solid sample.

2. The method of claim 1 wherein said separation step consists of filtering said combination to separate a filtrate comprising liquid and microorganisms from a substantial portion of said particulate sample.

3. The method of claim 1 wherein said non-toxic liquid comprises a solution of 0.5% to 6.0% NaCl in distilled water, said non-toxic liquid having a known light reduction effect on said luminescent microorganisms.

4. The method of claim 1 wherein said sample is selected from the group of particulate solids consisting of soils, sediments and sludges.

5. The method of claim 4 wherein said particulate solid material sample is obtained by centrifugation which separates at least a major portion of interstitial liquid from said particulate solid sample.

6. The method of claim 1 wherein a plurality of sample dilutions of varying known sample concentrations are combined with said microorganism suspension and the light outputs of said resultant filtrates are plotted against sample concentration to develop a dose-response curve for the determination of the concentration of said sample required to reduce the light output of the microorganisms by 50%.

7. The method of claim 6 wherein a plurality of sample dilutions of varying known concentration are prepared prior to contact with said microorganisms.

8. The method of claim 2 wherein said filtrate is separated from said combination through a filter having a pore size large enough to permit said microorganisms to pass and small enough to retain a substantial portion of said sample particles.

9. The method of claim 8 in which said filter pore size is between about 2 microns and about 50 microns.

10. The method of claim 9 wherein said filter pore size is about 35 microns.

11. The method of claim 1 wherein said combined sample and suspension are maintained in contact for a period of time sufficient to permit the microorganisms to be affected by any toxic substance which may be contained in said sample but not longer than about 20 minutes.

12. The method of claim 11 wherein said microorganisms are reconstituted lyophilized Photobacterium phosphorem and wherein said contact between said sample and said microorganism is carried out at a temperature of between about 15° C. and 30° C.

13. The method of claim 1 wherein said microorganisms are selected from the genera consisting of Photobacterium, Vibrio Lucibacterium, Achromobacter, Armillaria, Panus, Mycena, Omphalia and mixtures thereof.

* * * * *